United States Patent
Fattohi et al.

(10) Patent No.: US 7,749,527 B2
(45) Date of Patent: Jul. 6, 2010

(54) GEL COMPOSITIONS FOR CONTROL OF ECTO-PARASITES

(75) Inventors: Nahla Fattohi, Robbinsville, NJ (US); Debora L. Guido, Bordentown, NJ (US); Shobhan Sabnis, Pennington, NJ (US)

(73) Assignee: Wyeth LLC, Madison, NJ (US)

( * ) Notice: Subject to any disclaimer, the term of this patent is extended or adjusted under 35 U.S.C. 154(b) by 1085 days.

(21) Appl. No.: 11/435,659

(22) Filed: May 17, 2006

(65) Prior Publication Data

US 2006/0269584 A1   Nov. 30, 2006

Related U.S. Application Data

(60) Provisional application No. 60/684,202, filed on May 24, 2005.

(51) Int. Cl.
*A01N 25/24* (2006.01)
(52) U.S. Cl. .................. 424/407; 424/405; 514/522
(58) Field of Classification Search ............... 424/407, 424/405; 514/522
See application file for complete search history.

(56) References Cited

U.S. PATENT DOCUMENTS

| 5,543,573 | A | 8/1996 | Takagi et al. |
| 2004/0116419 | A1 | 6/2004 | Heaney et al. |
| 2004/0122075 | A1 | 6/2004 | Chiarello et al. |

FOREIGN PATENT DOCUMENTS

| WO | WO 2006/002984 | 1/2006 |
| WO | WO 2006/042099 | 4/2006 |

OTHER PUBLICATIONS

PCT International Preliminary Report on Patentability and Written Opinion of the International Searching Authority for corresponding PCT application No. PCT/US2006/019301, Nov. 30, 2007.

*Primary Examiner*—Johann R Richter
*Assistant Examiner*—Danielle Sullivan
(74) *Attorney, Agent, or Firm*—Joel B. Silver

(57) ABSTRACT

Semi-solid compositions comprising metaflumizone, a gelling agent and a non-aqueous solvent. The semi-solid compositions of this invention may be topically administered to animals, and are useful for preventing or treating, ectoparasitic infestations in warm-blooded animals for prolonged periods of time.

20 Claims, No Drawings

GEL COMPOSITIONS FOR CONTROL OF ECTO-PARASITES

This application claims priority from provisional Application No. 60/684,202, filed May 24, 2005, the entire disclosure of which is hereby incorporated by reference.

BACKGROUND OF THE INVENTION

Arthropod ectoparasites commonly infecting warm-blooded animals include ticks, mites, lice, fleas, blowfly, the ectoparasite *Lucilia* sp. of sheep, biting insects including keds (*Melophagus ovinus*) and migrating dipterous larvae such as *Hypoderma* sp. and *Dermatobia* in cattle, *Gastrophilus* in horses and *Cuterebra* sp. in rodents.

Metaflumizone is useful for the prevention and control of infestation by ectoparasites in warm-blooded animals. Topical administration of this active is a preferred method for administering this compound.

To provide suitable protection against ectoparasitic infection or infestation in warm-blooded animals it is desirable to use a semi-solid topical formulation having a relatively high loading of metaflumizone. Such a formulation has the effect of providing a formulation that is easy to apply, good spreading over skin, and avoids run-off. However, it is often difficult to formulate such compositions with stability of the active while maintaining the desirable characteristics of a semi-solid composition. Metaflumizone is one of several useful insecticidal agents which have found particular application for the control of fleas and ticks on animals, particularly companion animals such as dogs, cats and horses. It is particularly advantageous in that it can provide 4-6 weeks of protection from fleas and ticks in companion animals, yet it would still be desirable to formulate it so that a semi-solid application could be applied to protect the subject animal while avoiding the possibility of ingestion by the subject animal and/or run-off and waste of the active. Nonetheless, formulations are difficult due to the insolubility of metaflumizone in many solvents, and its instability in the presence of primary alcohols.

It is an object of the present invention to provide a semi-solid composition for topical administration which comprises a relatively high loading of metaflumizone and which will provide protection from ectoparasitic infestation for a suitable period of time.

It is also an object of the present invention to provide a method for preventing or treating ectoparasitic infestation in warm-blooded animals for prolonged periods of time.

It is another object of this invention to reduce or control the proliferation of such insects in warm-blooded animals for prolonged periods of time by a topically applied active, with the formulation being mild and gentle enough to avoid adverse skin reactions upon administration, yet with the ability to be retained in the animal's skin and/or coat over the time needed for protection.

These and other objects of the present invention will become more apparent from the description thereof set forth below and the appended claims.

SUMMARY OF THE INVENTION

The present invention provides semi-solid compositions for topical administration which comprise on a weight to weight basis:

from about 5% to about 30% of metaflumizone;
from about 1% to about 15% of a gelling agent;
from about 0% to about 8% of a surfactant;
from about 45% to about 80% of a non-aqueous solvent system.

The present invention further provides a method for preventing or treating ectoparasitic infection or infestation in a warm-blooded animal which method comprises topically administering to the animal an effective amount of the composition of this invention.

DETAILED DESCRIPTION OF THE INVENTION

In accordance with the present invention, the semi-solid compositions comprise metaflumizone, a gelling agent, and a non-aqueous solvent system. The invention also provides a method for preventing or treating acarid or arthropod ectoparasitic infection or infestation in warm-blooded animals, by topical application of the aforesaid formulations.

Preferred semi-solid compositions of this invention comprise on a weight-to-weight basis:

from about 5% to about 30% of metaflumizone;
from about 1% to about 15% of a gelling agent;
from about 0% to about 8% of a surfactant;
from about 45% to about 80% of a non-aqueous solvent system.

Preferred non-aqueous solvent systems are those wherein the solvent system comprises at least one, and preferably more than one non-aqueous solvent. Highly preferred solvents are those such as N,N diethyl-m-toluamid (DEET), γ-hexalactone (gamma-hexalactone), propylene glycol dicaprylate/dicaprate (commercially available as Miglyol 840), caprylic/capric/succinic triglyceride (commercially available as Miglyol 829), and caprylic/capric triglyceride (commercially available as Miglyol 812). An especially preferred combination of solvents comprises a mixture of approximately 7:1:2 ratio by weight of γ-hexalactone:N,N-diethyl-m-toluamide:Miglyol 840.

While not wishing to be bound by any particular theory, it is believed that the particular solvent system provides for a solution which can easily and effectively be gelled using a suitable gelling agent, and which provides a stable environment for the active metaflumizone while providing for it to be retained upon the animal's skin, hair, and be released over a period of time.

Uniquely, it has been found that semi-solid compositions using this solvent system can also retain relatively high loadings of metaflumizone so as to provide a relatively small volume of formulation to use as a rub-on, spot-on, squeeze-on or pour-on formulation. Advantageously, the rate of absorption of metaflumizone from a topical gel is controlled to achieve both long-lasting therapeutic efficacy, as well as resistance to elemental removal of the metaflumizone. The resultant length of efficacy is advantageous because animals are protected for a suitable period of time. Resistance to elemental removal is essential since most animals will be subject to the common elements of rain, bathing, sunlight etc. over the course of treatment, and removal of the metaflumazone would result in non-efficacy of the formulation.

Metaflumizone is described in U.S. Pat. No. 5,543,573, and U.S. Published Application 2004-0122075A1, both incorporated herein by reference. Chemically, it is known as (E Z)-2-[2-(4-cyanophenyl)-1-[3-(trifluoromethyl)phenyl]ethylidene]-N-[4-

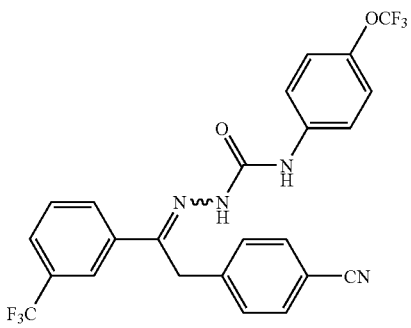

(trifluoromethoxy)phenyl]hydrazinecarboxamide.

Suitable gelling agents for use in the compositions of this invention include, but are not limited to, colloidal silicone dioxide, ethyl cellulose, methyl cellulose, methacrylic esters copolymers, carboxylated vinyl acetate terpolymer, polyvinylpropylene (PVP)/Vinyl acetate copolymers.

Typically, the gelling agent is utilized in the final formulation in an amount of about 1% to about 15% by weight/weight, with preferred amounts being in the range from about 2% to about 8%.

Suitable surfactants are those which are compatible with non-aqueous solvents, especially nonionic surfactants, with polysorbate 80 (polyoxyethylene 20 sorbitan monooleate) being an especially preferred surfactant. Other useful surfactants include non-ionic surfactants such as polyethylene glycol 660 hydroxystearate, polyoxyl 35 castor oil, or the like, esters (preferably fatty esters), and alkoxylated alcohols and esters. Among these, preferred are those such as alkoxylated fatty alcohol and alkoxylated nonylphenol, with ethoxylated fatty alcohols, including on average less than 20, more preferably, less than 15, ethylene oxide units per molecule. Preferably, the non-ionic surfactant is of low hygroscopicity so that at equilibrium, at 21° C. in air of 75% relative humidity, the surfactant takes up less than 25 g, more preferably, less than 20 g, of moisture per 100 g of the dry material, and at equilibrium, at 21° C. in air of 32% relative humidity, the ionic surfactant preferably takes up less than 10 g, more preferably less than 5 g, of moisture per 100 g of the dry material.

Preferred amounts of the surfactant range from about 0% to about 8%, with amounts in the range of from about 3-about 5% being especially preferred.

To manufacture the composition of the present invention, the metaflumizone is dissolved in the surfactant and solvent system, and then the gelling agent is added, with stirring. Use of a vacuum system is preferred since it provides a gel that is free of entrapped air.

An especially preferred semi-solid composition for topical administration to warm-blooded animals comprises, on a weight to weight basis, from about 50% to about 80% of a non-aqueous solvent system wherein the solvent system comprises approximately 7:1:2 ratio of gamma-hexalactone:N,N-diethyl-m-toluamide:Miglyol 840.

The compositions of this invention may further comprise other agents known in the art, such as an anti-syneresis agent, preservatives, colorants, antioxidants, and the like. Generally, these agents would be present in the compositions in an amount up to about 10% on a weight-to-weight basis. Typical anti-syneresis agents include those such as colloidal silicone dioxide and the ethyl cellulose. Typical preservatives are those such as methyl paraben, propyl paraben, benzalkonium chloride and thimerosal, or mixtures thereof, which can be used in conventional amounts. Other optional ingredients can also be incorporated, at levels well known to those skilled in the art.

Preferably, the compositions of the present invention are applied so as to effect a dosage in the range of 5-10 mg per Kg of body weight.

When topically administered, the compositions of this invention are highly effective for preventing or treating ectoparasitic infection and infestation for prolonged periods of time in warm-blooded animals such as, cattle, sheep, horses, camels, deer, swine, goats, dogs, cats, birds, and the like.

In order to facilitate a further understanding of the invention, the following examples are presented primarily for the purpose of illustrating specific embodiments thereof. The invention is not to be deemed limited thereby, except as defined in the claims.

EXAMPLE 1

Preparation of Metaflumizone Semi-Solid Composition A

| Ingredient | % w/w |
|---|---|
| Metaflumizone | 22.3 |
| Miglyol 840 | 12.5 |
| Colloidal silicone dioxide | 7.0 |
| Polysorbate 80 | 4.5 |
| Ethyl cellulose | 0.4 |
| Butylated hydrotoluene BHT | 0.2 |
| N,N-diethyl-m-toluamide (DEET) | 6.8 |
| γ-hexalactone | q.s. |
| Total | 100.0 |

The ethyl cellulose is dissolved in the γ-hexalactone by dispersing the powder slowly while mixing. To this is added the DEET, and then the metaflumizone is slowly added with stirring. The BHT and polysorbate 80 are added to the solution, and mixed to dissolve any solids. Then, the Miglyol 840 is added with stirring, followed by the colloidal silicone dioxide. Further mixing under vacuum results in the formation of a clear, yellow gel, free of entrapped air.

EXAMPLE 2

Preparation of Metaflumizone Semi-Solid Composition B

| Ingredient | % w/w |
|---|---|
| Metaflumizone | 23.6 |
| Miglyol 840 | 12.3 |
| Colloidal silicone dioxide | 31.1 |
| Polysorbate 80 | 4.4 |
| Ethyl cellulose | 0.4 |
| Butylated hydroxytoluene (BHT) | 0.2 |
| N,N-diethyl-m-toluamide (DEET) | 6.6 |
| γ-hexalactone | q.s. |
| Total | 100.0 |

Using the above ingredients according to the procedure of Example 1 results in the formation of a clear, yellow gel, free of entrapped air.

EXAMPLE 3

Preparation of Metaflumizone Semi-Solid Composition C

| Ingredient | % w/w |
|---|---|
| Metaflumizone | 23.44 |
| Miglyol 840 | 9.86 |
| Colloidal silicone dioxide | 4.50 |
| Polysorbate 80 | 4.53 |
| Ethyl cellulose | 0.40 |
| Butylated hydroxytoluene (BHT) | 0.24 |
| N,N-diethyl-m-toluamide (DEET) | 13.11 |
| γ-hexalactone | q.s. |
| Total | 100.0 |

Using the above ingredients according to the procedure of Example 1 results in the formation of a clear, yellow gel, free of entrapped air.

EXAMPLE 4

Horse Studies

To compare the duration of efficacy of the compositions of the present invention, a study is conducted on horses. Horses are infested with flies and then treated with the formulation by rubbing it on the head, back, and legs.

Specifically, a formulation containing 25% w/v metaflumizone gel prepared as in Example 1 was applied at a dose of 5 mg/kg (0.2 mL/10 kg as formulated) and compared to a commercially available fly repellent spray applied to cover the animal (~300 mL). Twenty-four horses were assigned randomly to three groups (untreated controls—Group A, commercial fly spray—Group B, metaflumizone gel—Group C). The results indicated that a longer duration of activity was produced using the metaflumizone gel versus a commercial fly spray.

Horn Fly Counts on Horses Administered Various Metaflumizone Formulations

| Group | n | Horn Fly Counts/Horse/Day (Geometric Means) | | | | | | | |
|---|---|---|---|---|---|---|---|---|---|
| | | −3 | −2 | 1 | 3 | 5 | 7 | 9 | 14 |
| A | 8 | 23.0 | 24.7 | 7.7 | 10.9 | 7.1 | 3.4 | 8.9 | 7.1 |
| B | 8 | 21.2 | 25.0 | 1.6 | 5.8 | 9.0 | 7.4 | 7.7 | 12.8 |
| | | % Efficacy | 78.8 | 47.1 | 0 | 0 | 13.6 | 0 | |
| C | 8 | 30.8 | 21.9 | 2.9 | 10.9 | 6.3 | 2.7 | 6.7 | 5.1 |
| | | % Efficacy | 62.7 | 0 | 12.2 | 21.5 | 24.7 | 28.0 | |

What is claimed is:

1. A composition for topical administration which comprises on a weight to weight basis
   from about 5% to about 30% of metaflumizone;
   from about 1% to about 15% of a gelling agent;
   from about 0% to about 8% of a surfactant; and
   from about 45% to about 80% of a non-aqueous solvent system.

2. The composition according to claim 1 which comprises from about 5% to about 20% of the metaflumizone compound.

3. The composition according to claim 1, which comprises from about 2% to 15% of the gelling agent.

4. The composition according to claim 2, which comprises from about 2% to 15% of the gelling agent.

5. The composition according to claim 1 wherein the gelling agent is selected from the group consisting of colloidal silicone dioxide, ethyl cellulose, methyl cellulose, methacrylic esters copolymers, carboxylated vinyl acetate terpolymer, PVP/Vinyl acetate copolymers or an equivalent non-aqueous solvent soluble polymer.

6. The composition according to claim 2 wherein the gelling agent is selected from the group consisting of colloidal silicone dioxide, ethyl cellulose, methyl cellulose, methacrylic esters copolymers, carboxylated vinyl acetate terpolymer, PVP/Vinyl acetate copolymers or an equivalent non-aqueous solvent soluble polymer.

7. The composition according to claim 1 wherein the surfactant is a non-ionic surfactant.

8. The composition according to claim 2 wherein the surfactant is a non-ionic surfactant.

9. The composition according to claim 1 wherein the surfactant is polyoxyothylene 20 sorbitan monooleate.

10. The composition according to claim 2 wherein the surfactant is polyoxyethylene 20 sorbitan monooleate.

11. The composition according to claim 1 wherein the amount of the surfactant is about 3% to about 5%.

12. The composition according to claim 2 wherein the amount of the surfactant is about 3% to about 5%.

13. The composition according to claim 1 wherein the solvent system comprises a mixture of approximately 7:1:2 ratio by weight of γ-hexalactone:N, N-diethyl-m-toluamide: propylene glycol dicaprylate/dicaprate.

14. The composition according to claim 2 wherein the solvent system comprises a mixture of approximately 7:1:2 ratio by weight of γ-hexalactone:N, N-diethyl-m-toluamide: propylene glycol dicaprylate/dicaprate.

15. The composition according to claim 1 which additionally contains up to about 8% by weight of one or more preservatives, colorants, antioxidants, or stabilizers.

16. The composition according to claim 1 which additionally includes an anti-syneresis agent.

17. A method for preventing or treating ectoparasitic infection or infestation in a warm-blooded animal which method comprises topically administering to the animal an ectoparasiticidally effective amount of a composition according to claim 1.

18. A method for preventing or treating ectoparasitic infection or infestation in a warm-blooded animal which method comprises topically administering to the animal an ectoparasiticidally effective amount of a composition according to claim 2.

19. The method according to claim 17 wherein the animal is selected from the group consisting of, a cow, a sheep, a horse, a camel, a deer, a swine, a goat, a dog, a cat, and a bird.

20. The method according to claim 18 wherein the animal is selected from the group consisting of a cow, a sheep, a horse, a camel, a deer, a swine, a goat, a dog, a cat, and a bird.

\* \* \* \* \*